(12) United States Patent
Guan et al.

(10) Patent No.: US 8,003,063 B2
(45) Date of Patent: Aug. 23, 2011

(54) MICROFLUIDIC DEVICES AND METHODS FOR MULTIPLE ANALYTE DETECTION

(75) Inventors: Xiaosheng Guan, Beijing (CN); Min Guo, Beijing (CN); Rong Zhang, Beijing (CN); Dong Dong, Beijing (CN); Yuming Hu, Beijing (CN); Ting Cui, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 84 days.

(21) Appl. No.: 12/516,999

(22) PCT Filed: Mar. 9, 2007

(86) PCT No.: PCT/CN2007/000757
§ 371 (c)(1),
(2), (4) Date: Nov. 24, 2009

(87) PCT Pub. No.: WO2008/083526
PCT Pub. Date: Jul. 17, 2008

(65) Prior Publication Data
US 2010/0068098 A1    Mar. 18, 2010

(30) Foreign Application Priority Data
Jan. 10, 2007    (CN) .......................... 2007 1 0063384

(51) Int. Cl.
*B01L 3/00* (2006.01)
(52) U.S. Cl. ....... 422/503; 422/504; 422/68.1; 436/180; 435/286.5; 137/14
(58) Field of Classification Search ............... 422/68.1, 422/503, 504; 435/286.5; 436/180; 137/14
See application file for complete search history.

(56) References Cited

U.S. PATENT DOCUMENTS

| 6,395,232 | B1 * | 5/2002 | McBride ............... 422/504 |
| 6,499,499 | B2 | 12/2002 | Dantsker et al. |
| 6,880,576 | B2 | 4/2005 | Karp et al. |
| 6,981,522 | B2 | 1/2006 | O'Connor et al. |
| 2002/0195463 | A1 * | 12/2002 | Seki et al. ............ 222/134 |
| 2003/0005967 | A1 * | 1/2003 | Karp ...................... 137/806 |

(Continued)

FOREIGN PATENT DOCUMENTS

CN        2702313        5/2005
(Continued)

OTHER PUBLICATIONS

International Search Report for PCT/CN2007/000757, mailed on Oct. 18, 2007, 6 pages.

(Continued)

*Primary Examiner* — In Suk Bullock
*Assistant Examiner* — Timothy G Kingan
(74) *Attorney, Agent, or Firm* — Morrison & Foerster LLP

(57) ABSTRACT

The invention is directed to microfluidic devices comprising at least two processing channels, wherein each of the processing channels comprises an inlet, an outlet, and a high-flow-resistant and hydrophilic conduit; a distributing channel, wherein the distributing channel comprises an upstream end and a downstream end, and is in fluid communication with each inlet of the processing channels via the high-flow-resistant and hydrophilic conduit; and a flushing channel, wherein the flushing channel comprises an upstream end and a downstream end, and is in fluid communication with each outlet of the processing channels. The invention also provides methods of using the microfluidic devices.

25 Claims, 5 Drawing Sheets

U.S. PATENT DOCUMENTS

| | | |
|---|---|---|
| 2004/0018117 A1* | 1/2004 | Desmond et al. ............... 422/64 |
| 2004/0209381 A1* | 10/2004 | Peters et al. .................. 436/177 |
| 2005/0089863 A1 | 4/2005 | Karlsen et al. |
| 2005/0118070 A1 | 6/2005 | Griss et al. |
| 2005/0133101 A1 | 6/2005 | Chung et al. |
| 2006/0210439 A1 | 9/2006 | Woudenberg et al. |
| 2007/0003443 A1 | 1/2007 | Sandell et al. |
| 2008/0223720 A1* | 9/2008 | Yamanaka et al. ............ 204/451 |

FOREIGN PATENT DOCUMENTS

| | | |
|---|---|---|
| CN | 1699984 | 11/2005 |
| CN | 1249431 | 4/2006 |
| CN | 1767899 | 5/2006 |
| CN | 1948966 | 4/2007 |
| WO | WO-03/052428 | 6/2003 |

OTHER PUBLICATIONS

International Preliminary Report on Patentability for PCT/CN2007/000757, issued on Jul. 14, 2009, 6 pages.

International Search Report for PCT/CN2007/000757, mailed on Oct. 18, 2007, 6 pages.

International Preliminary Report on Patentability for PCT/CN2007/000757, issued on Jul. 14, 2009, 6 pages.

* cited by examiner

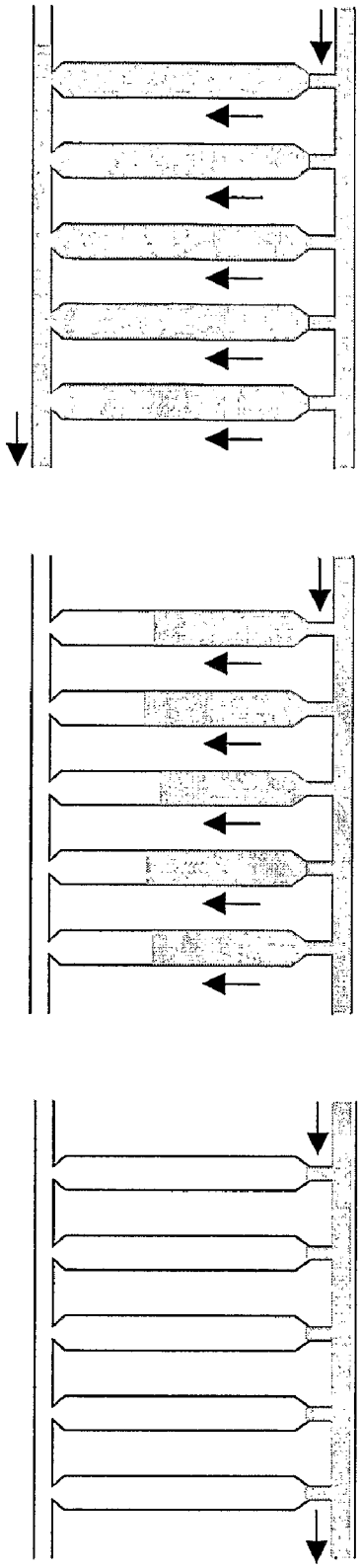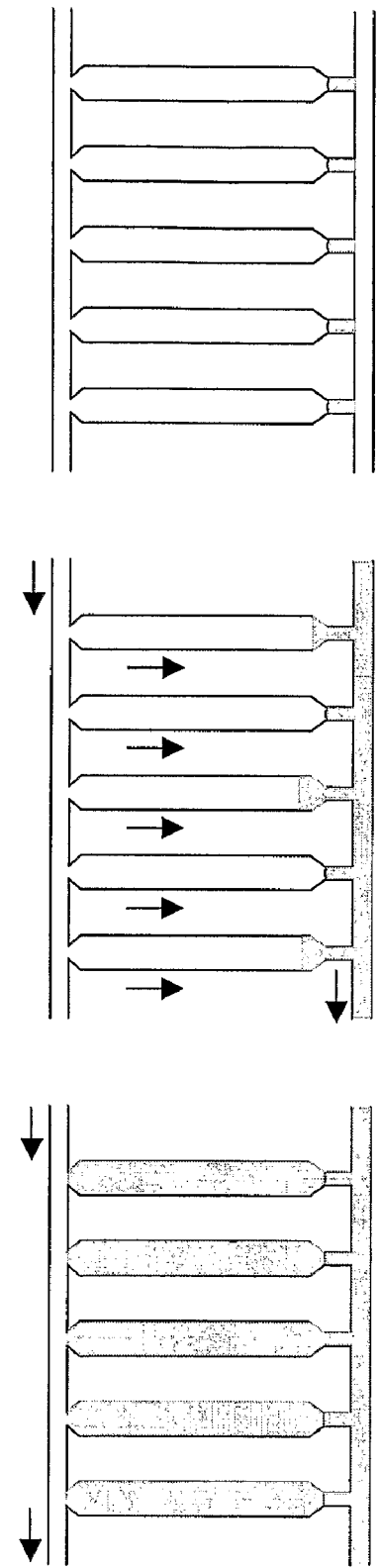
Fig. 3A  Fig. 3B  Fig. 3C  Fig. 3D  Fig. 3E  Fig. 3F

MICROFLUIDIC DEVICES AND METHODS FOR MULTIPLE ANALYTE DETECTION

Cross-Reference to Related Applications

This application is the national phase of PCT application PCT/CN2007/000757 having an international filing date of Mar. 9, 2007, which claims priority from China application number 200710063384.1 filed Jan. 10, 2007. The contents of these documents are incorporated herein by this reference in their entirety.

FIELD OF THE INVENTION

The invention pertains generally to devices for use in microfluidic control and automatic multiple sample processing in parallel.

BACKGROUND OF THE INVENTION

High throughput is one of many advantages and goals of Micro-Total-Analysis-Systems or Lab-on-a-Chip systems. High throughput often means either assaying multiple samples at one time or conducting multiple assays for one sample, or both. For the case of assaying multiple samples at one time, processing simultaneously or in parallel is a basic requirement for valid data analysis and result comparisons. For a typical biological assay, each sample is further subject to multiple steps of processing before its characteristics or compositions being determined. These steps include, but not limited to, reaction, separation, dilution, purification, extraction, washing, mixing, etc. Each of the steps may involve a different reagent or buffer fluid that is common to all samples.

Clearly, it is more efficient to distribute common fluids to different multiple processing units in parallel than to fill them one by one. For a multiplexed assay, different samples or reagent fluids may be loaded at first to each of the multiple processing units, or, different reagents may be deposited in advance to the multiple processing units in dry form. Reactions in the processing channels may be either homogeneous (e.g., RT-PCR) or heterogeneous (e.g., a microarray assay). For multi-step protocols (e.g., most immunoassay protocols), more than one common reagent fluids may be applied in sequence, and a common fluid is desirable to be 'flushed' (i.e., fluid being emptied and air being introduced) before next fluid is introduced. Air may be applied between any two common liquid fluids. It is desirable that the flushing process be in parallel through the multiple processing units to avoid potential shortcut.

When multiple processing units are delivered and emptied with fluid for many times, air bubbles may be formed and trapped because it is practically impossible for fluids to be flowed in an exactly synchronous fashion within the multiple processing units. Any slight flow imbalance could easily add up each time and quickly disrupt the concurrence in the multiple processing units. The flow imbalance may be resulted from inexactness of geometry among multiple processing units, and is further complicated by random surface effect, particularly in the presence of air bubbles once formed.

Various microfluidic systems have been developed for improving fluid control in multi-channeled high throughput processes. In some systems, a cascading channel-splitting structure is provided to make the paths from each of the multiple processing units to a common fluid source equidistantly. It has been further known that a fluidic flow may randomly choose one branch over the other at a channel split owing to surface effect. Therefore, ever-decreasing channel dimensions towards the last level of cascading is often practiced so that corresponding ever-increasing flow resistance would help overcome the surface effect experienced at upper levels of channel-splitting. However, such a structure works poorly as it is flushed by air, because it is very difficult to expel any liquid fluid out of the smallest capillaries in a channeled fluidic network. As number of common fluids increases, each with its own cascading channel-splitting structure so as to avoid flushing by air, undesirable cross intersection of channels occurs if they are put on the same 2-D plane. In order to solve this problem, a rather complex multi-layered fluid distributing structure has been developed. See, e.g., U.S. Pat. Nos. 6,880,576 and 6,981,522. These two patents disclose microfluidic devices with multiple fluid process regions for subjecting similar samples to different process conditions in parallel. In these devices, one or more common fluid inputs may be provided to minimize the number of external fluid supply components. U.S. Pat. No. 6,499,499 discloses an elevated flow resistance microfluidic structure and method thereof to distribute a fluid into multiple channels in parallel, which, however, is insufficient to accomplish further repetitive flushing and distributing steps in parallel for multi-step assays. The U.S. Patent application 2006210439-A1 discloses a method in which a fluidic device is pre-vacuumed and a common sample fluid is then made possible to autonomously occupy multiple dead-end processing channels, however, the task of emptying channels in parallel is very difficult, if not totally impossible, with the dead-end microfluidic structure, hence a multi-step assays cannot be readily achieved. There remains a need to develop a microfluidic device to efficiently delivering and emptying multiple processing channels in parallel.

All patents, patent applications, and publications cited herein are hereby incorporated by reference in their entirety.

BRIEF SUMMARY OF THE INVENTION

The present invention provides microfluidic devices and methods of use thereof, for example, to accomplish the task of both delivering and emptying multiple processing channels in parallel.

In one aspect, the invention provides a microfluidic device comprising: at least two processing channels, wherein each of the processing channels comprises an inlet, an outlet, and a high-flow-resistant and hydrophilic conduit; a distributing channel, wherein the distributing channel comprises an upstream end and a downstream end, and is in fluid communication with each inlet of the processing channels via the high-flow-resistant and hydrophilic conduit; and a flushing channel, wherein the flushing channel comprises an upstream end and a downstream end, and is in fluid communication with each outlet of the processing channels.

In another aspect, the invention provides a method of delivering a common aqueous fluid in multiple processing channels in parallel, comprising: (a) providing a microfluidic device described herein; (b) applying a positive pressure at the upstream end of the distributing channel or a negative pressure at the downstream end of the distributing channel while the upstream end of the distributing channel is connected to a common aqueous fluid until all of the high-flow-resistant and hydrophilic conduits are in communication with the common aqueous fluid in the distributing channel; (c) keeping the downstream end of the distributing channel and the upstream end of the flushing channel closed to fluid flow, and upstream end of the distributing channel and the downstream end of the flushing channel open to fluid flow; and (d) applying a positive pressure at the upstream end of the distributing channel or a negative pressure at the downstream end of the flushing channel, whereby the common aqueous fluid is introduced into the processing channels via the high-flow-resistant and hydrophilic conduit.

In another aspect, the invention provides of removing aqueous fluid in multiple processing channels in parallel, comprising: (a) providing a microfluidic device described herein, wherein the processing channels are filled with aqueous fluids; (b) applying a positive pressure at the upstream end of the flushing channel or a negative pressure at the downstream end of the flushing channel to empty a fluid from the flushing channel; (c) keeping the downstream end of the flushing channel and the upstream end of the distributing channel closed to fluid flow, and upstream end of the flushing channel and the downstream end of the distributing channel open to fluid flow; and (d) applying a positive pressure at the upstream end of the flushing channel or a negative pressure at the downstream end of the distributing channel, whereby the aqueous fluid from the processing channels are emptied.

BRIEF DESCRIPTION OF THE DRAWINGS

FIG. 2A shows that during sample loading from the loading ports, and the sample fluid cannot move into the distributing channel because of the nature of the high-flow-resistant and hydrophilic conduits. The loading step can be performed manually with use of a pipeting instrument, or automatically with use of a pump creating a negative pressure at downstream end of the flushing channel. In the latter case, the loading ports may be further attached with means that are in fluid communication with separate sample or reagent fluid reservoirs as shown in FIG. 2B. For example, this embodiment may be used in a multiplexed competitive immunoassay where separate antigen samples are first mixed with a common competitive antibody solution. The first common aqueous fluid may be simultaneously aspirated into the processing channel after it fills the distributing channel. The sample loading ports may be closed after sample loading.

FIGS. 3A-3C are schematic diagrams of fluid delivering process. The individual sample or reagent loading ports are omitted for clarity. FIG. 3A shows that the distributing channel is first filled with a common fluid, and by capillary force the fluid also enters all the high-flow-resistant and hydrophilic conduits, but not any further into the processing channels. In FIG. 3B, a sufficiently large pressure differential is established between the distributing channel and the flushing channel, allowing the fluid breaking and continuing to flow through an arbitrary high-flow-resistant and hydrophilic conduit. The large pressure differential allows achieving a parallel flow and helps overcome any adverse capillary forces that may be exerted by various geometry or surface property changes along the paths from inlet to outlet, which would otherwise randomly blocks fluid flow in some processing channels. Because of inexactness of fabrication, the fluid flows in the processing channels are unlikely at exactly the same speed, as sketched in FIG. 3B. Complete filling of all processing channels can be accomplished by the established large pressure differential. FIG. 3C shows that air initially occupying the processing channels has been totally displaced by the incoming fluid, and the incoming fluid is entering into the flushing channel towards the downstream end of the flushing channel.

FIGS. 3D-3F are schematic diagrams of fluid emptying process. The individual sample or reagent loading ports are omitted for clarity. FIG. 3D shows that fluid is first emptied from the flushing channel. FIG. 3E shows fluids are being emptied from the multiple processing channels by flowing backward from outlet to inlet in all processing channels. Approaching to the end of fluid emptying process, fluid trailing meniscus arrives earlier at the high-flow-resistant and hydrophilic conduits in those processing channels where fluid flows relatively faster, producing a strong adverse capillary force. The adverse capillary force prevents the fluid from being displaced out of the high-flow-resistant and hydrophilic conduits by the incoming air; thereby creating a 'valving' effect that helps maintain a sufficient pressure differential between the distributing channel and the flushing channel. This valving effect is crucial in that the incoming air can keep pushing the rest fluid out of those relatively slower flowing processing channels. FIG. 3F shows the end of the fluid emptying process, where all processing channels are completely emptied, leaving only a tiny amount of fluid in all high-flow-resistant and hydrophilic conduits because of the effect of hydrophilicity.

DETAILED DESCRIPTION OF THE INVENTION

Figure 1:
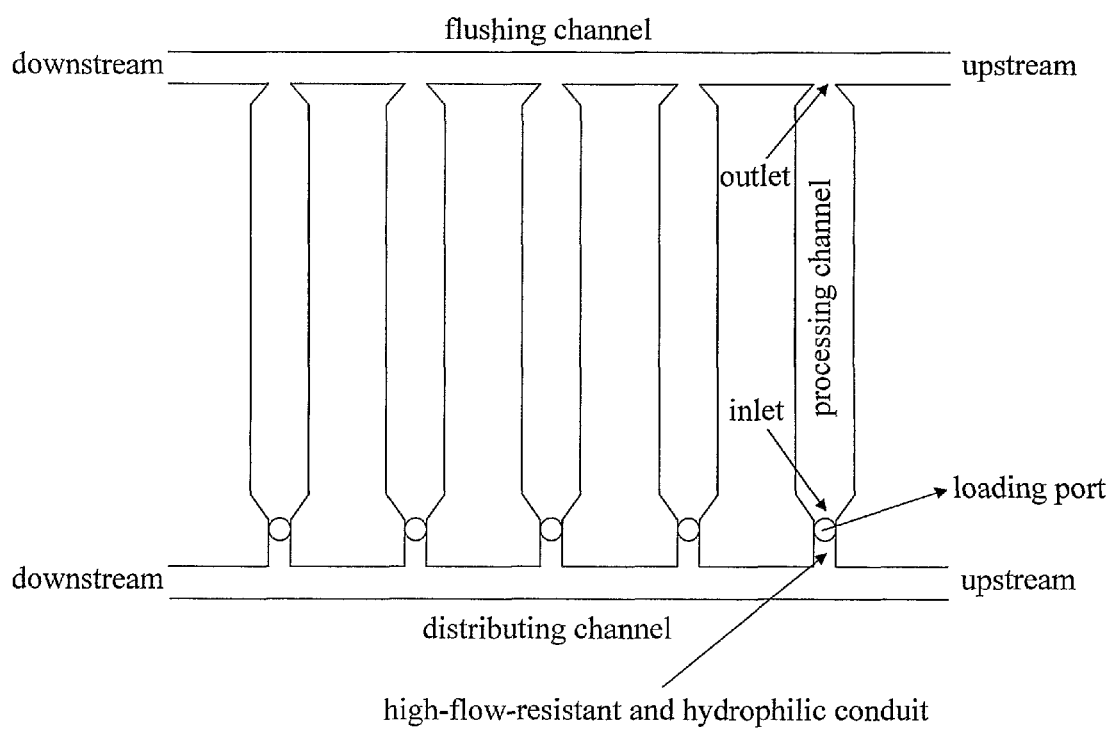
FIG. 1 is a diagram showing an example of a microfluidic device which has five processing channels.
Figure 2B:
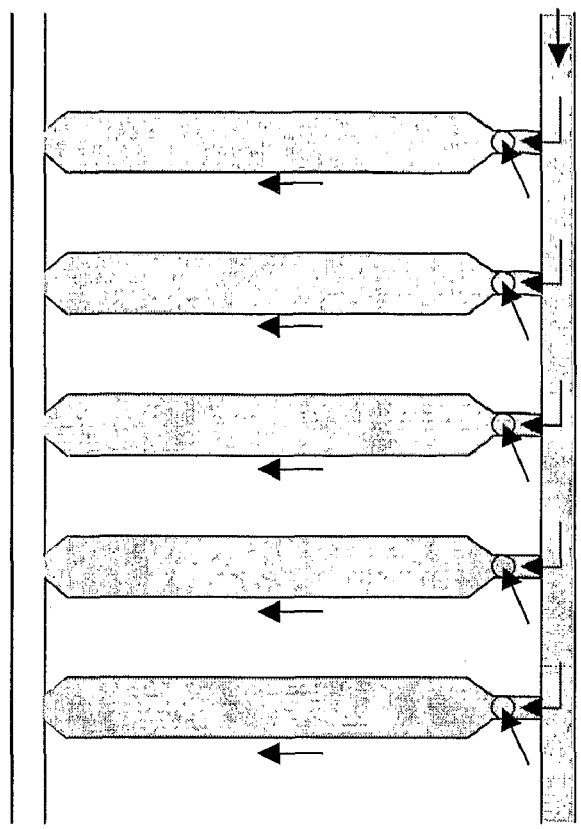
FIGS. 2A-2B are schematic diagrams showing a sample loading process.
Figure 2A:
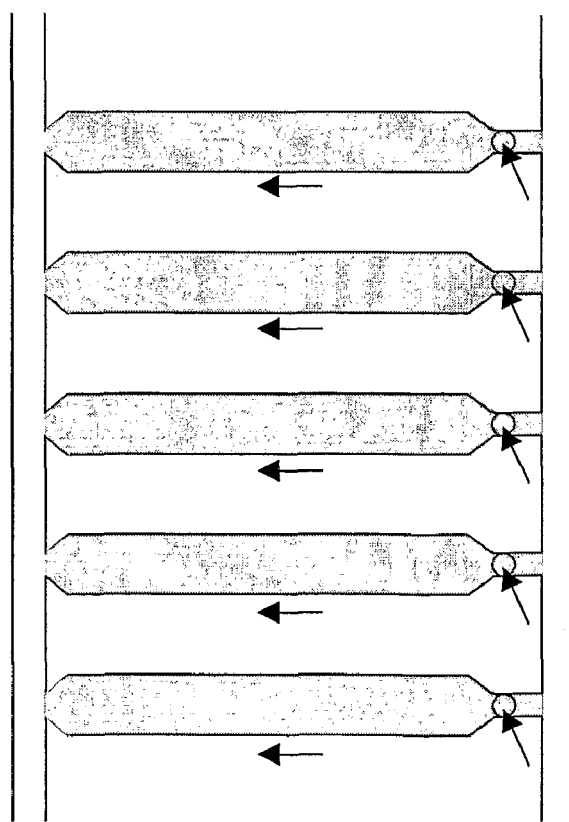
Figure 4:
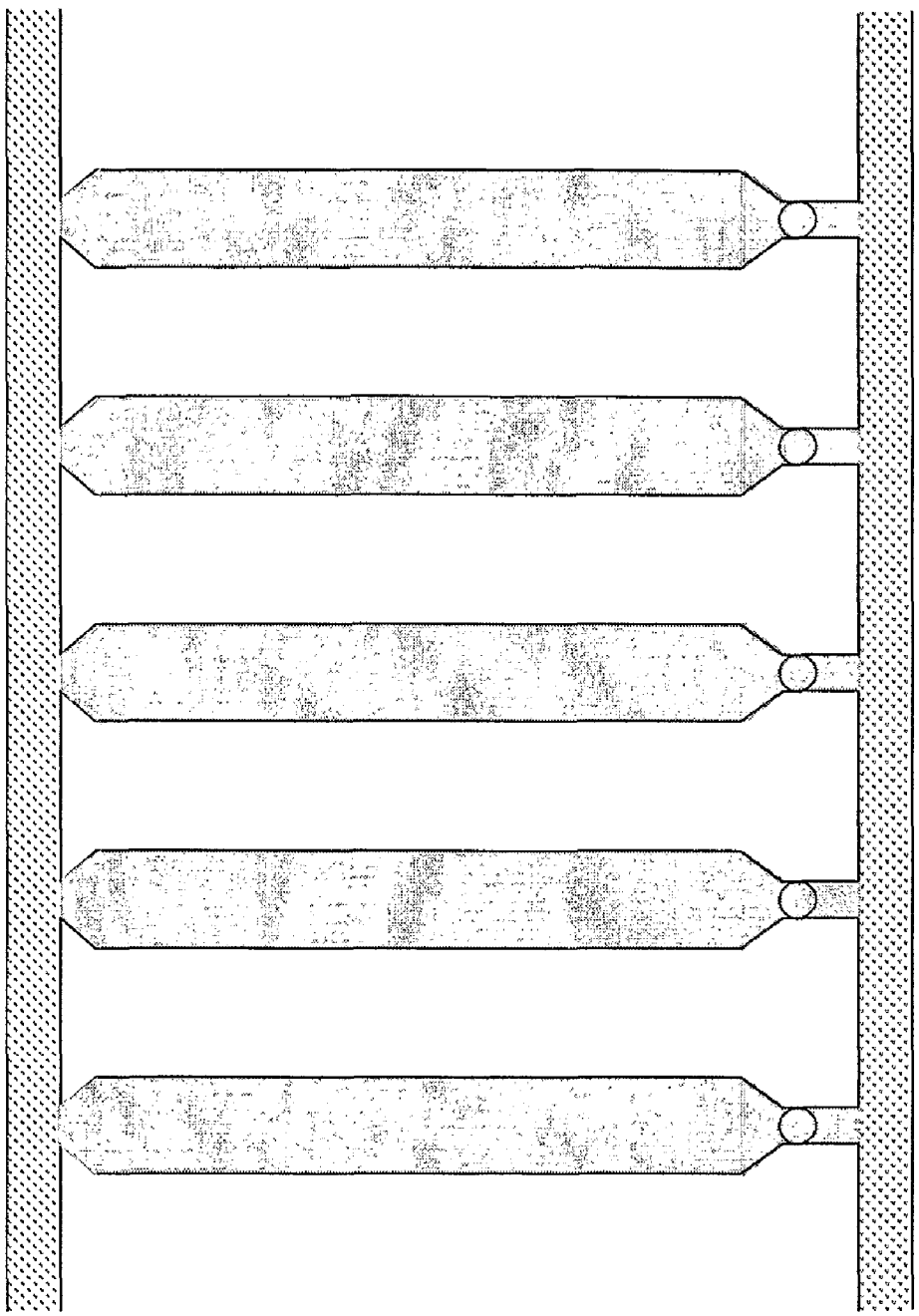
FIG. 4 shows that immediately after the multiple processing channels are filled with aqueous fluids, the distributing and flushing channels may optionally be filled with an immiscible and inert fluid with a purpose to effectively isolate the processing channels from one another, thus eliminating cross contamination during a multiplexed reaction that follows.

The invention provides microfluidic devices comprising: at least two processing channels, wherein each of the processing channels comprises an inlet, an outlet, and a high-flow-resistant and hydrophilic conduit; a distributing channel, wherein the distributing channel comprises an upstream end and a downstream end, and is in fluid communication with each inlet of the processing channels via the high-flow-resistant and hydrophilic conduit; and a flushing channel, wherein the flushing channel comprises an upstream end and a downstream end, and is in fluid communication with each outlet of the processing channels.

In some embodiments, each of the processing channels further comprises an aqueous fluid loading port which is at a location where the high-flow-resistant and hydrophilic conduit connects with the processing channel inlet. In some embodiments, capillary sippers may be attached to the loading ports at one end, and at the other end, the sippers could be open to any type of fluid sources, including microtitter plates, vials, cuvettes, or even fabricated wells. This provides a means of automatic individual sample or reagent loading by using vacuum connected downstream of the flushing channel.

The micro fluidic devices of the invention comprises at least two processing channels. In some embodiments, the device comprises at least three, at least four, at least five, at least six, at least seven, at least eight, at least nine, at least ten, at least eleven, or at least twelve processing channels.

Various ways provided by U.S. Pat. No. 6,499,499 for increasing flow resistance may be used for making the high-flow-resistant and hydrophilic conduit. For example, altering the geometry (e.g., dimensions or configuration) of the channels and/or adding porous or other flow reducing materials to fluid circuits may be used to increase flow resistance.

In some embodiments, the inner dimension of the high-flow-resistant and hydrophilic conduit is about 100 microns or less, about 50 microns or less, or about 10 microns or less. The dimension of the high-flow-resistant and hydrophilic conduit and/or the processing channels may not be the same through out each channel. In some embodiments, the ratio of the smallest inner dimension of the high-flow-resistant and hydrophilic conduit over the smallest inner dimension of the processing channel is about ½ or less, about ⅕ or less, or ¹⁄₁₀ or less. In some embodiments, the inner surface of the high-flow-resistant and hydrophilic conduit has a water contact angle of about 85° or less, about 45° or less, or about 15° or less.

Microfluidic devices described herein may be fabricated in various ways using a wide variety of materials. For example, glass, silicon, silicon nitride, quartz, or similar materials may be used. Various conventional machining or micromachining techniques such as those known in the semiconductor industry may be used to fashion channels, chambers, and/or apertures. Other techniques such as embossing, stamping, molding, and soft lithography may also be used. Attachment techniques (e.g., thermal, chemical, light-activated bonding, and mechanical attachment) may also be used if more than one layer of materials need to be assembled together.

The invention also provides methods of using the microfluidic devices for performing any type of bioassays in parallel, such as assays involving protein-protein interactions, nucleic acid interactions, any other type of biomolecule interactions. Exemplary assays that the devices may be used for include immunoassays (e.g., direct, sandwiched, competitive assays), PCR reactions (including non-isothermal and isothermal type of thermal cycling), and enzymatic assays.

The microfluidic devices of the invention may be used for delivering a common aqueous fluid into multiple processing channels in parallel. First, the common aqueous fluid is introduced into the distributing channel from the upstream end to the downstream end of the distributing channel by applying a positive pressure at the upstream end of the distributing channel or a negative pressure at the downstream end of the distributing channel of a microfluidic device while the upstream end of the distributing channel is connected to the common aqueous fluid until all of the high-flow-resistant and hydrophilic conduits are in communication with a common aqueous fluid in the distributing channel. In this step, the upstream end and the downstream end of the flushing channel may be open or closed. Second, the downstream end of the distributing channel and the upstream end of the flushing channel are kept closed, and the upstream end of the distributing channel and the downstream end of the flushing channel are kept open. Closing of the downstream end of the distributing channel and the upstream end of the flushing channel and opening of the upstream end of the distributing channel and the downstream end of the flushing channel may be performed simultaneously or in any order. Third, a positive pressure is applied at the upstream end of the distributing channel or a negative pressure is applied at the downstream end of the flushing channel to introduce the common aqueous fluid to the processing channels via the high-flow-resistant and hydrophilic conduit.

Aqueous fluids (such as samples) may be loaded into the processing channels through the loading ports, for example, loaded by positive pressure or negative pressure. The aqueous fluids may be loaded before or after delivering the common aqueous fluid. The loading ports can be closed after loading the aqueous liquids before next fluid operation step.

The methods of the invention may include a step of blocking fluid communication between the processing channels by loading a liquid immiscible and inert to the common aqueous fluid into the distributing channel and the flushing channel from their respective upstream end to the downstream end by positive pressure or negative pressure. In some embodiments, the blocking step is performed immediately after delivering the common aqueous fluid into the processing channels. In some embodiments, the blocking step is performed immediately after loading the aqueous fluids into the processing channels through the loading ports. Any liquid that is immiscible and inert to the common aqueous fluid may be used. For example, paraffin oil, mineral oil, and fluorinated fluid may be used.

In some embodiments, the common aqueous fluid comprises a buffer for washing, dilution, hybridization, or detection in a bioassay. In some embodiments, the aqueous fluids loaded through the loading ports contain nucleic acid and/or proteins.

The invention also provides methods of removing aqueous fluid in multiple processing channels in parallel. First, a positive pressure is applied at the upstream end of the flushing channel or a negative pressure is applied at the downstream end of the flushing channel to empty a fluid from the flushing channel. This fluid may be aqueous fluid, or may be immiscible and inert to the common aqueous fluid in the processing channels. In this step, the upstream end and the downstream end of the distributing channel may be open or closed. Second, the downstream end of the flushing channel and the upstream end of the distributing channel are kept closed, and the upstream end of the flushing channel and the downstream end of the distributing channel are kept opened. The closing and the opening step may be performed simultaneously, or in either order. Third, a positive pressure is applied at the upstream end of the flushing channel or a negative pressure is applied at the downstream end of the distributing channel to empty aqueous fluid from the processing channels.

Fabrication of Microfluidic Devices

Figure 5:
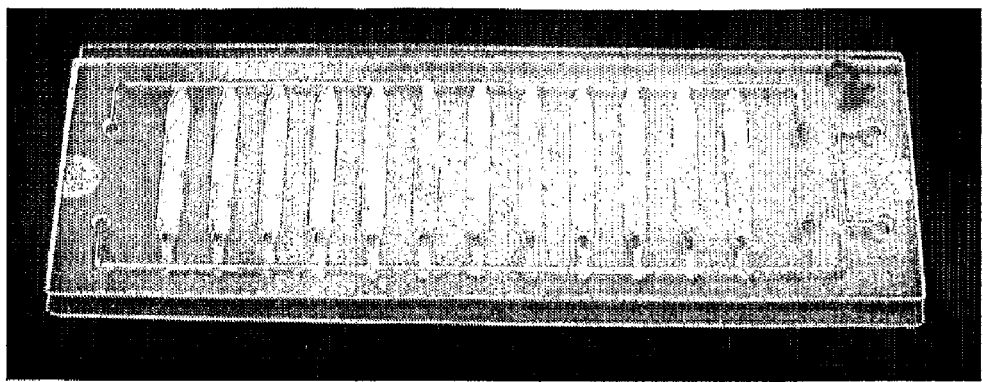
FIG. 5 shows a design of multiplexed microfluidic chip for immunoassays.

FIG. 5 shows an example of a multiplexed microfluidic chip that can be used for immunoassays. The chip is a simple two-piece device: a polymethylmethacrylate (PMMA) substrate and a glass slide bonded together. The microfluidic channels were machined in the upper PMMA piece, while 12 protein arrays were pre-spotted on the lower glass piece and were in alignment with 12 processing channels in the PMMA piece. The distributing channel has three fluid inlets at its upstream end on the right, and one outlet at its downstream end on the left. The flushing channel has one inlet at its upstream end on the right, and one outlet at its downstream end on the left. At the inlet of each of processing channels there is a sample loading port. Between the loading ports and the distributing channel there are the high-flow-resistant and hydrophilic conduits. These conduits have a depth of only 10 microns, while other channels are of 300-500 microns in depth.

To use the device, for example, sample fluids were loaded by a pipette through the loading ports. The sample fluids were incubated under a condition to allow reaction with protein arrays in each processing channel, e.g., through antigen-antibody binding reaction.

After the reaction, the sample fluids were first emptied by applying a positive pressure at the upstream end of the flushing channel or a negative pressure at the downstream end of the flushing channel to empty any fluid from the flushing channel, and then applying a positive pressure at the upstream end of the flushing channel or a negative pressure at the downstream end of the distributing channel while the downstream end of the flushing channel and the upstream end of the distributing channel have been closed and the downstream end of the distributing channel has been opened, while aqueous fluid from the processing channels are emptied. The processing channels were washed 3 times with a washing buffer by performing the process of delivering a common aqueous fluid to the processing channels and removing aqueous fluid in multiple processing channels described herein. A secondary antibody reagent was flowed in using the common aqueous fluid delivering process, which stayed for a while in the processing channels before it was emptied as described above. Then, the channels were washed again 3 times with the same washing buffer. Finally, a buffer containing an enzymatic substrate was introduced into the processing channels to induce a chemiluminescence's reaction at the protein arrays, which was detected by CCD camera. Signals collected were further subject to data analysis.

Although the foregoing invention has been described in some detail by way of illustration and examples for purposes of clarity and understanding, it will be apparent to those skilled in the art that certain changes and modifications may be practiced. Therefore, descriptions and examples should not be construed as limiting the scope of the invention, which is delineated by the appended claims.

What is claimed is:

1. A microfluidic device comprising:
   1) at least two processing channels, wherein each of the processing channels comprises an inlet, an outlet, and a high-flow-resistant and hydrophilic conduit, wherein each of the processing channels further comprises an aqueous fluid loading port which is at a location where the high-flow-resistant and hydrophilic conduit connects with the processing channel inlet; and
   2) a distributing channel, wherein the distributing channel comprises an upstream end and a downstream end, and is in fluid communication with each inlet of the processing channels via the high-flow-resistant and hydrophilic conduit; and
   3) a flushing channel, wherein the flushing channel comprises an upstream end and a downstream end, and is in fluid communication with each outlet of the processing channels.

2. The microfluidic device of claim 1, wherein the inner dimension of the high-flow-resistant and hydrophilic conduit is 10 microns or less.

3. The microfluidic device of claim 1, wherein the inner dimension of the high-flow-resistant and hydrophilic conduit is 50 microns or less.

4. The microfluidic device of claim 1, wherein the inner dimension of the high-flow-resistant and hydrophilic conduit is 100 microns or less.

5. The microfluidic device of claim 1, wherein the ratio of the smallest inner dimension of the high-flow-resistant and hydrophilic conduit over the smallest inner dimension of the processing channel is ½ or less.

6. The microfluidic device of claim 1, wherein the ratio of the smallest inner dimension of the high-flow-resistant and hydrophilic conduit over the smallest inner dimension of the processing channel is ⅕ or less.

7. The microfluidic device of claim 1, wherein the ratio of the smallest inner dimension of the high-flow-resistant and hydrophilic conduit over the smallest inner dimension of the processing channel is 1/10 or less.

8. The microfluidic device of claim 1, wherein the inner surface of the high-flow-resistant and hydrophilic conduit has a water contact angle of 85° or less than 85°.

9. The microfluidic device of claim 1, wherein the inner surface of the high-flow-resistant and hydrophilic conduit has a water contact angle of 45° or less than 45°.

10. The microfluidic device of claim 1, wherein the inner surface of the high-flow-resistant and hydrophilic conduit has a water contact angle of 15° or less than 15°.

11. A method of delivering a common aqueous fluid in multiple processing channels in parallel, comprising:
    (a) providing a microfluidic device according to claim 1;
    (b) applying a positive pressure at the upstream end of the distributing channel or a negative pressure at the downstream end of the distributing channel while the upstream end of the distributing channel is connected to a common aqueous fluid until all of the high-flow-resistant and hydrophilic conduits are in communication with the common aqueous fluid in the distributing channel;
    (c) keeping the downstream end of the distributing channel and the upstream end of the flushing channel closed to fluid flow, and upstream end of the distributing channel and the downstream end of the flushing channel open to fluid flow; and
    (d) applying a positive pressure at the upstream end of the distributing channel or a negative pressure at the downstream end of the flushing channel, whereby the common aqueous fluid is introduced into the processing channels via the high-flow-resistant and hydrophilic conduit.

12. The method of claim 11, further comprising a step of loading aqueous fluids to the processing channels through the loading ports by positive pressure or negative pressure.

13. The method of claim 12, wherein the aqueous fluids are loaded before delivering the common aqueous fluid to the processing channels.

14. The method of claim 12, wherein the aqueous fluids are loaded while delivering the common aqueous fluid to the processing channels.

15. The method of claim 12, wherein the loading ports are closed after loading the aqueous liquids before next fluid operation step.

16. The method of claim 11, further comprising a step of blocking fluid communication between the processing channels, wherein a liquid which is immiscible and inert to the common aqueous fluid is loaded into the distributing channel and the flushing channel from their respective upstream end to the downstream end by positive pressure or negative pressure.

17. The method of claim 16, wherein the blocking step is performed immediately after delivering the common aqueous fluid into the processing channels.

18. The method of claim 12, further comprising a step of blocking fluid communication between the processing channels, wherein a liquid which is immiscible and inert to the common aqueous fluid is loaded into the distributing channel and the flushing channel from their respective upstream end to downstream end by positive pressure or negative pressure, wherein the blocking step is performed immediately after loading the aqueous fluids into the processing channels through the loading ports.

19. The method of claim 16, wherein the immiscible and inert liquid is selected from the group consisting of paraffin oil, mineral oil, and fluorinated fluid.

20. The method of claim 11, wherein the common aqueous fluid comprises a buffer for washing, dilution, hybridization, or detection.

21. The method of claim 11, wherein aqueous fluids loaded through the loading ports contain nucleic acid and/or protein molecules.

22. A method of removing aqueous fluid in multiple processing channels in parallel, the method comprising:
    (a) providing a microfluidic device according to claim 1, wherein the processing channels are filled with aqueous fluids;

(b) applying a positive pressure at the upstream end of the flushing channel or a negative pressure at the downstream end of the flushing channel to empty a fluid from the flushing channel;

(c) keeping the downstream end of the flushing channel and the upstream end of the distributing channel closed to fluid flow, and upstream end of the flushing channel and the downstream end of the distributing channel open to fluid flow; and (d) applying a positive pressure at the upstream end of the flushing channel or a negative pressure at the downstream end of the distributing channel, whereby the aqueous fluid from the processing channels are emptied.

23. The method of claim 22, wherein the fluid in step (b) is an aqueous fluid.

24. The method of claim 22, wherein the fluid in step (b) is a fluid immiscible and inert fluid to the aqueous fluids in the processing channels.

25. The method of claim 18, wherein the immiscible and inert liquid is selected from the group consisting of paraffin oil, mineral oil, and fluorinated fluid.

* * * * *